US00PP27543P2

(12) United States Plant Patent
Zaiger et al.

(10) Patent No.: US PP27,543 P2
(45) Date of Patent: Jan. 17, 2017

(54) INTERSPECIFIC TREE NAMED 'AUTUMN MAGIC'

(50) Latin Name: ***Interspecific Prunus* species**
Varietal Denomination: Autumn Magic

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 23 days.

(21) Appl. No.: 14/545,943

(22) Filed: Jul. 10, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with an attractive dark red skin color.
2. Fruit with good storage and shipping quality.
3. Fruit with good flavor and eating quality.
4. Fruit maturing in the late season.
5. Tree with vigorous, upright growth habit.

1 Drawing Sheet

Botanical designation: Interspecific *Prunus* species.
Variety denomination: 'Autumn Magic'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Flavorfall' Interspecific (U.S. Plant Pat. No. 11,990), 'Spicezee' Interspecific (U.S. Plant Pat. No. 13,503), 'Fall Fiesta' Interspecific (U.S. Plant Pat. No. 22,428) and our proprietary non-patented interspecific seedlings with the field identification numbers '28MF660', '32M146', '65Z400', '30M591' and '62LG300'.

STATEMENT REGARDING FEDERALLY SPONSORED RESEARCH AND DEVELOPMENT

Not applicable.

ORIGIN OF THE VARIETY

The new and distinct interspecific tree consists of *Prunus salicina, Prunus armeniaca, Prunus persica* and *Prunus*

*persica* var. *nucipersica*. It was originated by us in our experimental orchard located near Modesto, Calif. as an open pollinated seedling selection from our proprietary non-patented interspecific seedling '28MF660'. The seed parent '28MF660' is a first generation seedling from the cross of our non-patented proprietary interspecific seedlings '32M146' and '30M591'. '32M146' is a first generation seedling from the cross of our proprietary seedling '65Z400' and 'Spicezee' Interspecific (U.S. Plant Pat. No. 13,503). '30M591' is a first generation seedling from the cross of our proprietary seedling '62LG300' and 'Flavorfall' Interspecific (U.S. Plant Pat. No. 11,990). A large number of these open pollinated seedlings were budded onto older established trees of 'Nemaguard' Rootstock (non-patented) to enhance earlier fruit production. Under close and careful observation the present budded seedling exhibited desirable fruit and tree characteristics and was selected in 2012 for additional asexual propagation and commercialization.

ASEXUAL REPRODUCTION OF THE VARIETY

In 2012 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree, which consists of Plum, Apricot, Peach and Nectarine has vigorous, upright growth and is a regular and productive bearer of large size fruit with an attractive dark red skin color. The fruit is further characterized by its firm flesh, good flavor and eating quality with good storage and shipping ability. In comparison to its seed parent (28MF660) the fruit of the new variety has darker red skin, sets a more consistent crop and is 6 days earlier in maturity. In comparison to the commercial variety 'Fall Fiesta' Interspecific (U.S. Plant Pat. No. 22,428) the fruit of the new variety is approximately 25 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 4 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright, usually pruned to vase shape.

*Branch habit*.—Upright, crotch angle approximately 35°, increases with heavy crop load.

*Productivity*.—Productive, thinning and spacing of fruit necessary for marketable size fruit. Number of fruit set varies with climatic conditions during blooming period.

*Bearer*.—Regular, has had adequate fruit set 3 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 750 hours at or below 45° F.

Trunk:

*Size*.—Large, average circumference 38.1 cm at 25.4 cm above ground on a 4 year old tree.

*Stocky*.—Medium stocky.

*Texture*.—Medium shaggy, roughness increases with age.

*Color*.—Varies from 2.5Y 7/2 to 2.5Y 5/2.

Branches:

*Size*.—Medium. Average circumference 8.7 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 51 in a 25.8 square cm section of branch. Average length 3.1 mm. Average width 0.9 mm. Color varies from 2.5Y 5/4 to 2.5Y 4/2.

*Color*.—New growth varies from 5GY 5/8 to 7.5YR 3/6. Mature growth varies from 7.5YR 4/2 to 10YR 3/2, varies with age of growth.

Leaves:

*Size*.—Small to medium. Average length 91.0 mm. Average width 42.8 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth except for small ridges created by midrib and pinnate venation. Both upper and lower surfaces glabrous.

*Petiole*.—Small to medium. Average length 14.2 mm. Average width 1.4 mm. Longitudinally grooved. Surface glabrous. Color varies from 2.5GY 6/6 to 5GY 6/6.

*Glands*.—Type — globose. Number varies from 2 to 3, average number 3. Size — small. Average length 1.2 mm. Average width 0.6 mm. Located primarily on the upper portion of the petiole and the base of the leaf blade. Color varies from 5GY 5/6 to 7.5R 3/4.

*Stipules*.—Average number 2. Average length 9.9 mm. Margin — pectinate. Color varies from 2.5GY 6/4 to 5GY 5/6.

*Color*.—Upper surface varies from 7.5GY 3/4 to 7.5GY 2/4. Lower surface varies from 5GY 5/4 to 5GY 4/4. Midvein color varies from 2.5GY 8/4 to 5GY 8/4.

Flower buds:

*Size*.—Medium to large. Average length 11.2 mm. Average diameter 6.5 mm.

*Hardiness*.—Hardy with respect to California winters.

*Density*.—Medium.

*Form*.—Conical, becoming elongated just before opening.

*Pedicel*.—Average length 8.3 mm. Average width 0.8 mm. Surface glabrous. Color varies from 2.5GY 6/8 to 5GY 6/6.

*Color*.—N 9.5/(white).

*Number of buds per spur*.—Varies from 7 to 10, average number 8.

Flowers:

*Blooming period*.—Date of First Bloom Feb. 12, 2014. Date of Petal Fall Feb. 22, 2014, varies slightly with climatic conditions.

*Size*.—Medium to large. Average height 10.1 mm. Average diameter 24.9 mm.

*Petals*.—Normally 5, alternately arranged to sepals. Petal apex — rounded. Petal base — rounded to somewhat truncated. Size — medium to large. Average length 10.3 mm. Average width 22.8 mm. Form — elliptical. Arrangement — free. Margin — sinuate. Color N 9.5/(white). Both upper and lower surfaces glabrous.

*Sepals*.—Normally 5, alternately arranged to the petals. Size — medium. Average length 3.4 mm. Average width 2.7 mm. Shape — ovate. Apex rounded to triangular. Margin — entire. Both upper and lower surfaces glabrous. Color — upper surface varies from 5GY 6/8 to 7.5GY 6/8. Lower surface varies from 5GY 5/6 to 7.5GY 6/6.

*Stamens*.—Average number per flower 28. Average filament length 8.2 mm. On average, the stamens are above the height of the petals. Filament color N 9.5/(white). Anther color varies from 10R 4/10 to 5Y 8/8.

*Pollen*.—Self-sterile, pollinator required. Color varies from 5Y 7/8 to 5Y 7/10.

*Pistil*.—Number — normally 1. Surface — glabrous. Average length 9.8 mm. Position of stigma an average of 1.7 mm below anthers. Color varies from 10Y 8/6 to 2.5GY 8/6.

*Fragrance*.—Heavy.

*Color*.—N 9.5/(white).

*Pedicel*.—Average length 11.3 mm. Average width 0.8 mm. Color varies from 2.5GY 6/6 to 2.5GY 6/8.

*Number flowers per flower bud*.—Average number 2, varies from 1 to 4.

Fruit:

*Maturity when described*.—Firm ripe and ready for consumption.

*Date of first picking*.—Oct. 2, 2014.

*Date of last picking*.—Oct. 11, 2014, varies slightly with climatic conditions.

*Size*.—Large. Average diameter axially 60.2 mm. Average transversely in suture plane 62.7 mm. Average weight 150.5 grams, varies slightly with fertility of the soil, amount of thinning and climatic conditions.

*Form*.—Globose.

*Suture*.—Lipped, extends from base to apex.

*Ventral surface*.—Lipped.

*Apex*.—Nearly round.

*Base*.—Flat.

*Stem cavity*.—Rounded to slightly elongated in suture plane. Average depth 7.1 mm. Average breadth 4.9 mm.

Stem:

*Size*.—Small to medium. Average length 10.5 mm. Average diameter 2.6 mm.

*Color*.—Varies from 5GY 5/8 to 7.5YR 3/6.

Flesh:

*Ripens*.—Evenly.

*Texture*.—Firm, meaty.

*Fibers*.—Few, small, tender.

*Firmness*.—Firm, comparable to standard varieties.

*Aroma*.—Slight.

*Amydgalin*.—Undetected.

*Eating quality*.—Excellent.

*Flavor*.—Good balance between acid and sugar.

*Juice*.—Moderate amount, enhances flavor.

*Acidity*.—Not available.

*Brix*.—Average Brix 21.0°, varies slightly with amount of fruit per tree and climatic conditions.

*Color*.—Varies from 2.5Y 8.5/8 to 2.5Y 8/8.

*Pit cavity*.—Average length 24.5 mm. Average width 22.3 mm. Average depth 7.1 mm. Color varies from 2.5Y 8/8 to 7.5R 3/12.

Skin:

*Thickness*.—Medium.

*Surface*.—Smooth to slightly undulated.

*Bloom*.—Moderate amount, complete coverage.

*Tendency to crack*.—None.

*Color*.—Ground color varies from 2.5Y 9/2 to 2.5Y 9/4. Overspread with 2.5R 2/2 to 5R 2/2.

*Tenacity*.—Tenacious to flesh.

*Astringency*.—Slight to none.

Stone:

*Type*.—Clingstone, medium adherence.

*Size*.—Medium. Average length 23.5 mm. Average width 21.3 mm. Average thickness 12.1 mm.

*Form*.—Ovoid.

*Base*.—Flat.

*Apex*.—Pointed. Average length 2.1 mm.

*Surface*.—Pitted throughout.

*Sides*.—Unequal, one side extending further outward from suture plane.

*Ridges*.—Very narrow, small ridge near groove on each side of suture, extends from base to apex.

*Tendency to split*.—None.

*Color*.—Varies from 7.5YR 5/6 to 10YR 4/4 when dry.

Kernel:

*Size*.—Small to medium. Average length 14.4 mm. Average width 10.4 mm. Average depth 5.3 mm.

*Viability*.—Viable, complete embryo development.

*Skin color*.—Varies from 7.5YR 4/6 to 10YR 4/4.

Use:

*Dessert*.—Market — local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

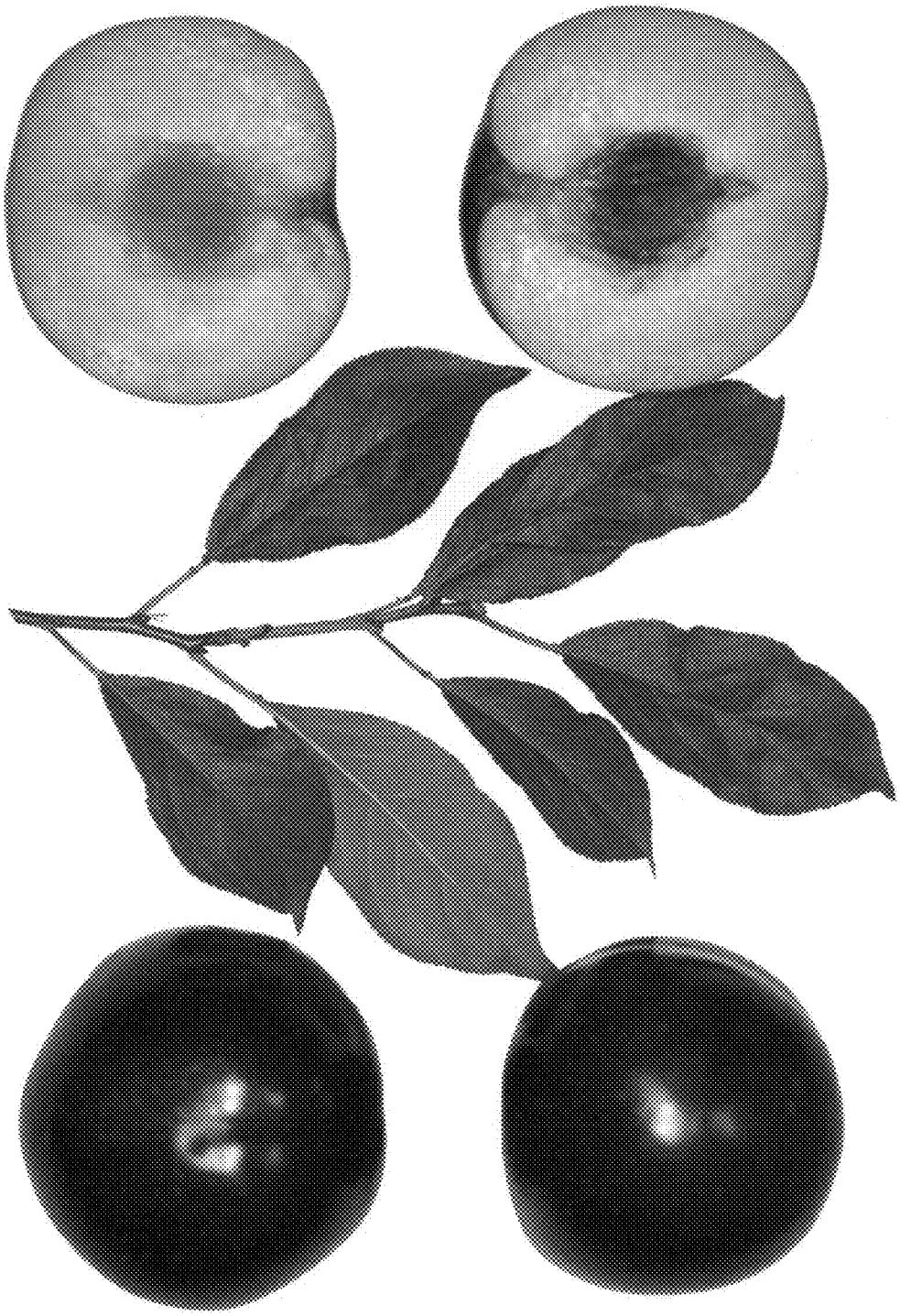

* * * * *